(12) United States Patent
Smith et al.

(10) Patent No.: US 6,213,128 B1
(45) Date of Patent: Apr. 10, 2001

(54) APPARATUS AND METHOD FOR MAKING AND INSPECTING MULTI-COMPONENT WRAPPED ARTICLE

(75) Inventors: Barry Scott Smith, Hopewell; Michael J. Mullins, Chesterfield, both of VA (US)

(73) Assignee: Philip Morris Incorporated, New York, NY (US)

( * ) Notice: Subject to any disclaimer, the term of this patent is extended or adjusted under 35 U.S.C. 154(b) by 0 days.

(21) Appl. No.: 09/325,355

(22) Filed: Jun. 4, 1999

(51) Int. Cl.$^7$ ..................................... A24C 5/32
(52) U.S. Cl. ............... 131/280; 131/84.1; 131/905; 131/906; 131/907; 131/908; 131/29; 131/46; 131/65; 131/76; 131/91; 131/88
(58) Field of Search .................. 131/280, 84.1, 131/905, 906, 907, 908, 29, 46, 65, 76, 91, 88

(56) References Cited

U.S. PATENT DOCUMENTS

| | | |
|---|---|---|
| 3,464,421 * | 9/1969 | Pinkham ................. 131/61 |
| 4,001,579 | 1/1977 | Lebet et al. . |
| 4,212,541 | 7/1980 | Ducommun et al. . |
| 4,976,544 | 12/1990 | Neri . |
| 4,986,285 | 1/1991 | Radzio et al. . |
| 5,010,904 | 4/1991 | Lassiter . |
| 5,013,905 | 5/1991 | Neri . |
| 5,095,204 * | 3/1992 | Novini ................. 250/223 |
| 5,235,649 | 8/1993 | Reda . |
| 5,366,096 | 11/1994 | Miller . |
| 5,388,594 | 2/1995 | Counts et al. . |
| 5,414,270 | 5/1995 | Henderson et al. . |

* cited by examiner

*Primary Examiner*—Stanley S. Silverman
*Assistant Examiner*—Mark Halpern
(74) *Attorney, Agent, or Firm*—Burns, Doane, Swecker & Mathis, L.L.P.

(57) ABSTRACT

In an apparatus for making and inspecting a multi-component cigarettes, each cigarette including two or more different components arranged relative to one another, the apparatus includes a device for advancing a web in a first direction. The apparatus further includes a device for positioning at least two different components of a cigarette relative to one another on the web as the web advances in the first direction. The apparatus further includes a garniture device for wrapping the web around the at least two different components by moving opposite edges of the web transversely to the first direction such that, at a closure point in the garniture device, the opposite edges overlap each other. The apparatus further includes an imaging device disposed upstream of the closure point for generating an image of the at least two different components. The apparatus further includes a processing device connected to the imaging device for comparing the generated image with a reference standard and determining if the generated image deviates from the reference standard. A method for manufacturing and inspecting multicomponent articles is also disclosed.

30 Claims, 5 Drawing Sheets

APPARATUS AND METHOD FOR MAKING AND INSPECTING MULTI-COMPONENT WRAPPED ARTICLE

BACKGROUND AND SUMMARY OF THE INVENTION

The present invention relates to a system and method for making and inspecting of multi-component wrapped articles; more specifically, to a system and a method for the optical inspection, registration, and rejection of cigarettes on an open garniture combiner.

A well-known filter cigarette 21 structure is shown in FIG. 1. A rod 23 of tobacco is manufactured on a commercially available cigarette machine; e.g. those manufactured by Molins PLC, and others. The tobacco rod 23 is, in its simplest form, a column of cut tobacco filler 25 wrapped in a paper wrapper 27 held in place by a longitudinal adhesive seam 29. A filter 31 included with the cigarette 21 is manufactured by gathering a length of cellulose acetate, treating the cellulose acetate and forming a cylindrical filter element or plug 33, and encasing the filter element in "plug wrap" 35.

As seen in FIG. 2, in a typical manufacturing process for the tobacco rod 23, the paper wrapper 27 in the form of a continuous web is moved at high speed in the direction of arrow 37, herein referred to as the wrapping direction, toward a so-called garniture section 39 of a cigarette making machine. The tobacco filler 25 is deposited on the wrapper 27 prior to the garniture section 39. The garniture section 39 typically includes a first end 41 that is flat or slightly curved and upwardly open, a second end 43 in the form of a sleeve with a hole equal to the diameter of the cigarette 21, and a curved surface 45 connecting the first and second ends. The garniture section 39 is designed to curl the moving paper wrapper 27 around the tobacco rod 23, i.e., in a direction transverse to the wrapping direction 37 as the wrapper moves in the wrapping direction. Preferably, before encountering the garniture section 39, the wrapping paper 27 is already curling upwards to fit against the inner surface 45 of the garniture section. Closure of the wrapper 27 around the tobacco filler 25 to form the rod 23 occurs at the exit 43 of the garniture section 39 where the rod exits through the hole. The continuous rod 23 is subsequently cut at some downstream point C to form a tobacco rod 23 of a desired length.

There are numerous methods known for joining the cut tobacco rod 23 to the filter 31. As seen in FIG. 3, a common method of joining the rod 23 and the filter 31 involves "tipping" a double-length rod of tobacco 23 with filters 31 adjacent to both ends of the rod and cutting the rod in half to yield two filter cigarettes. The filters 31 are connected to the tobacco rod 23 by an overwrap of paper 47 called "tipping paper". Generally, the handling of the filters 31, cut tobacco rods 23, and finished cigarette 21 during the combining step is handled by vacuum rollers (not shown). The components fit into flutes on the outside periphery of the rollers and are held in place by an applied vacuum force as they are moved from place to place.

The final products are given an exterior inspection, such as discussed in U.S. Pat. Nos. 5,235,649, 5,366,096, 5,414,270, 5,013,905 and 4,976,544. Such prior art inspections involve optical inspection with a video camera. The image is fed into a digital computer; then the image is analyzed for the presence of defects. Other inspections, such as density inspections, may also be made by exposing the cigarette or rod to various forms of electromagnetic radiation, such as in U.S. Pat. Nos. 5,010,904, 4,001,579, 4,986,285 and 4,212,541. The prior art inspection systems are not typically concerned with relative placement of internal components of the cigarette, because the tobacco rod 23 and the filter 31 typically abut.

The development of new types of cigarettes, such as those in U.S. Pat. No. 5,388,594 which has multiple internal components disposed at precise distances from one another, requires the development of new inspection systems. Cigarettes according to the '594 patent contain a tobacco plug, a hollow void chamber, a hollow acetate tube, and a filter. The relative positioning of the interior components of these cigarettes is crucial to their proper operation and must be carefully maintained. It may happen that, in the manufacturing of such cigarettes, machine settings will require adjustment to maintain consistent placement of components.

Visual inspection of the final product to determine the relative placement of components is impossible according to the prior art inspection systems without manually disassembling the finished cigarette due to the various layers paper or other material surrounding the components. Such disassembly would likely disturb the interior spacing and would, in any event, occur too late in the manufacturing process to provide useful feedback for correcting machine settings in a timely manner.

The present invention provides a solution to the problem of ensuring that the intended structure of multi-component cigarettes is maintained within design specifications by providing for optical inspection of the multi-component cigarette, preferably within a garniture section prior to closure of a wrapping paper. The present invention also permits providing for the rejection of cigarettes that do not meet specified requirements.

In accordance with one aspect of the present invention, an apparatus for making and inspecting a multi-component cigarettes, each cigarette including two or more different components arranged relative to one another, is provided. The apparatus includes a device for advancing a web in a first direction. The apparatus further includes a device for positioning at least two different components of a cigarette relative to one another on the web as the web advances in the first direction. The apparatus further includes a garniture device for wrapping the web around the at least two different components by moving opposite edges of the web transversely to the first direction such that, at a closure point in the garniture device, the opposite edges overlap each other. The apparatus further includes an imaging device disposed upstream of the closure point for generating an image of the at least two different components. The apparatus further includes a processing device connected to the imaging device for comparing the generated image with a reference standard and determining if the generated image deviates from the reference standard.

In accordance with another aspect of the present invention, an apparatus for making and inspecting a multi-component articles, each article including two or more components arranged relative to one another, is provided. The apparatus includes a device for arranging two or more components of a multi-component article relative to one another. The apparatus further includes an imaging device arranged relative to the arranging device for generating an image of the components of the multi-component articles. The apparatus further includes a processing device connected to the imaging device for comparing the generated image with a reference standard and determining if the generated image deviates from the reference standard.

In accordance with another aspect of the present invention, a method for making and inspecting a multicomponent cigarettes, each cigarette including two or more different components arranged relative to one another, is provided. According to the method, a web is advanced in a first direction, and at least two different components of a cigarette are positioned relative to one another on the web as the web advances in the first direction. The web is wrapped around the at least two different components by moving opposite edges of the web transversely to the first direction with a garniture device such that, at a closure point in the garniture device, the opposite edges overlap each other. An image of the at least two different components is generated with an imaging device disposed upstream of the closure point. The generated image is compared with a reference standard and it is determined if the generated image deviates from the reference standard with a processing device.

According to still another aspect of the present invention, a method of making and inspecting a multi-component article is disclosed. According to the method, a plurality of components are arranged relative to one another. An image of the arranged components is generated with an imaging device. The generated image is compared with a reference standard. It is determined if the generated image deviates from the reference standard.

BRIEF DESCRIPTION OF THE DRAWINGS

The features and advantages of the present invention are well understood by reading the following detailed description in conjunction with the drawings in which like numerals indicate similar elements and in which.

DETAILED DESCRIOTION

Figure 1:
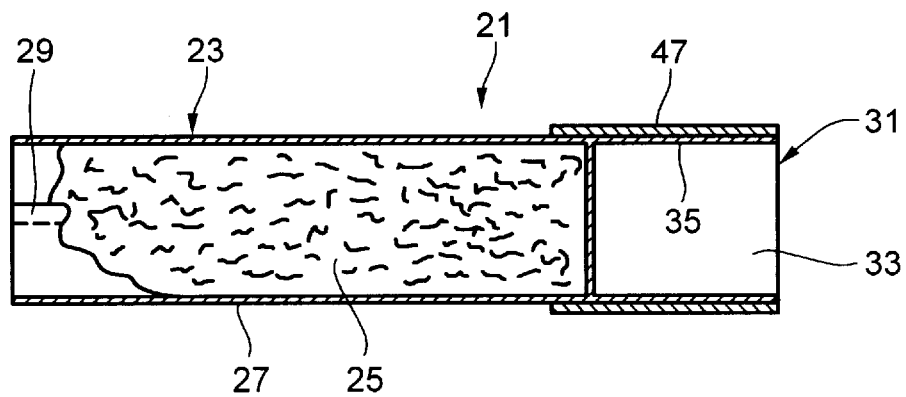
FIG. 1 is a schematic, partially cross-sectional side view of a conventional filter cigarette according to the prior art.
Figure 2:
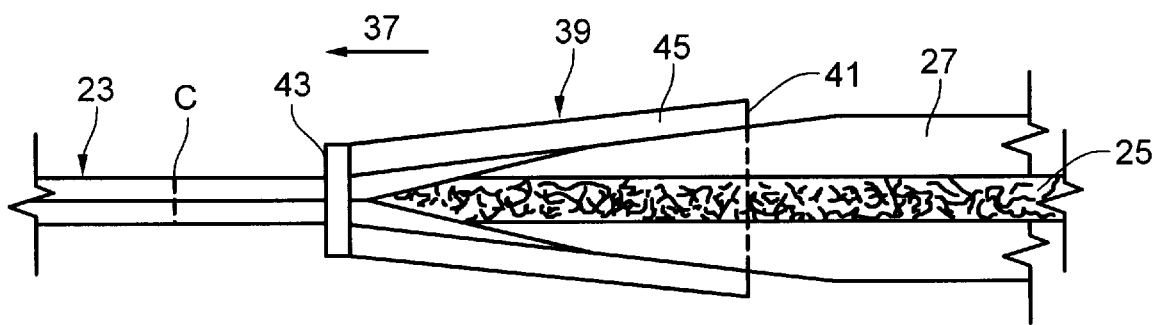
FIG. 2 is a schematic, top view of manufacturing equipment showing the wrapping of a tobacco rod with wrapping paper according to the prior art.
Figure 3:
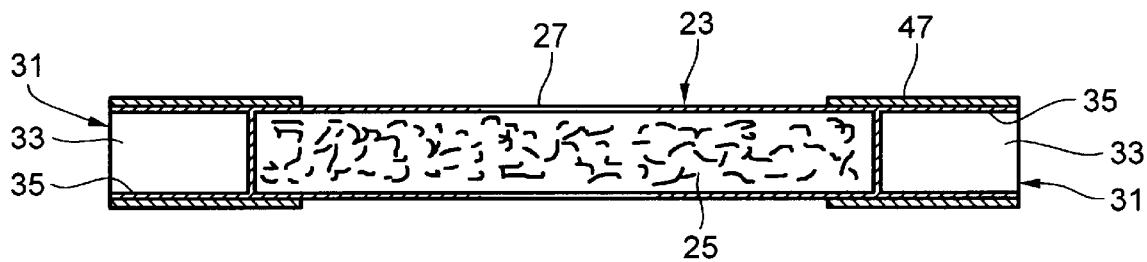
FIG. 3 is a schematic, cross-sectional side view of a wrapped double-length tobacco rod tipped on both ends with conventional filters prior to being cut to length to form a conventional filter cigarette according to the prior art.
Figure 4:
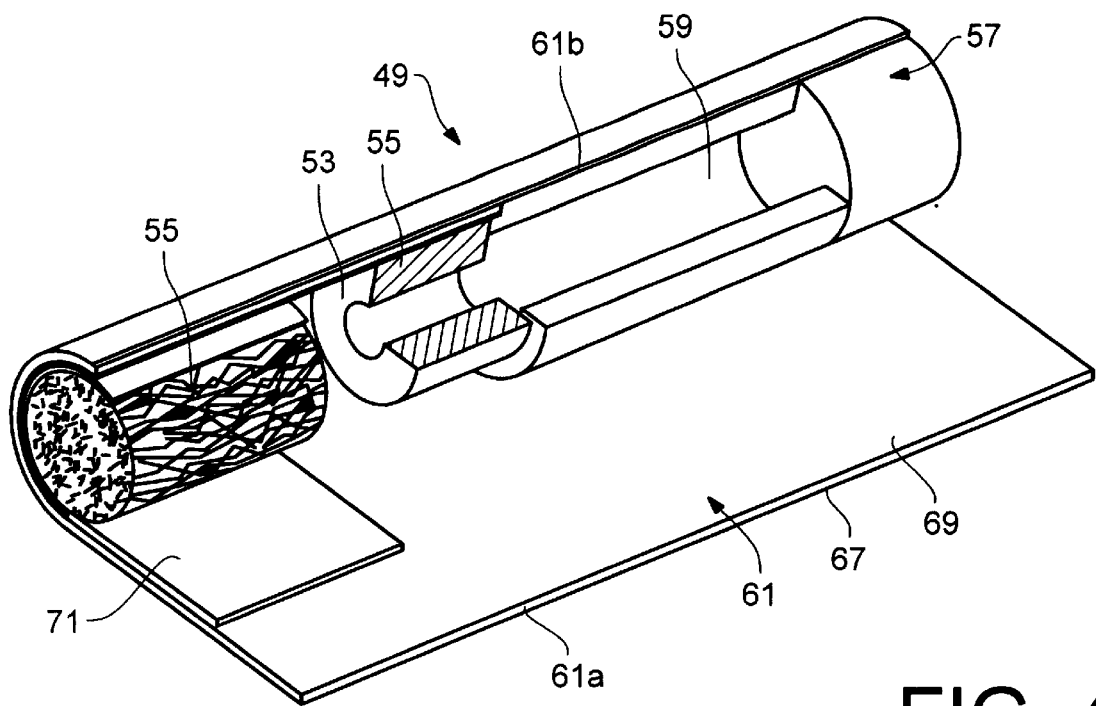
FIG. 4 is a schematic, partially cut-away, perspective view of a multi-component cigarette.

Operation of the apparatus and method according to the present invention will be described with reference to its use in making and inspecting a multicomponent cigarette 49 similar to the cigarette disclosed in U.S. Pat. No. 5,388,594, the disclosure of which is incorporated herein in its entirety. FIG. 4 illustrates the preferred components of the cigarette 49, including a tobacco plug 51, a hollow void chamber 53, a hollow acetate tube 55, a mouthpiece filter 57 having a hollow portion 59, and paper 61, preferably including several different wrapping papers, overwrapping the components. The cigarette 49 is not, however, limited to containing these components. For example, the apparatus and method according to the present invention could, if desired or necessary, be used in connection with the manufacture and inspection of a conventional cigarette 21 such as was described previously. Moreover, the present invention is not limited to the manufacture and inspection of cigarettes, and may be applicable to the manufacture and inspection of other structures, particularly those that require inspection of components prior to wrapping or enclosing of the components.

Figure 5:
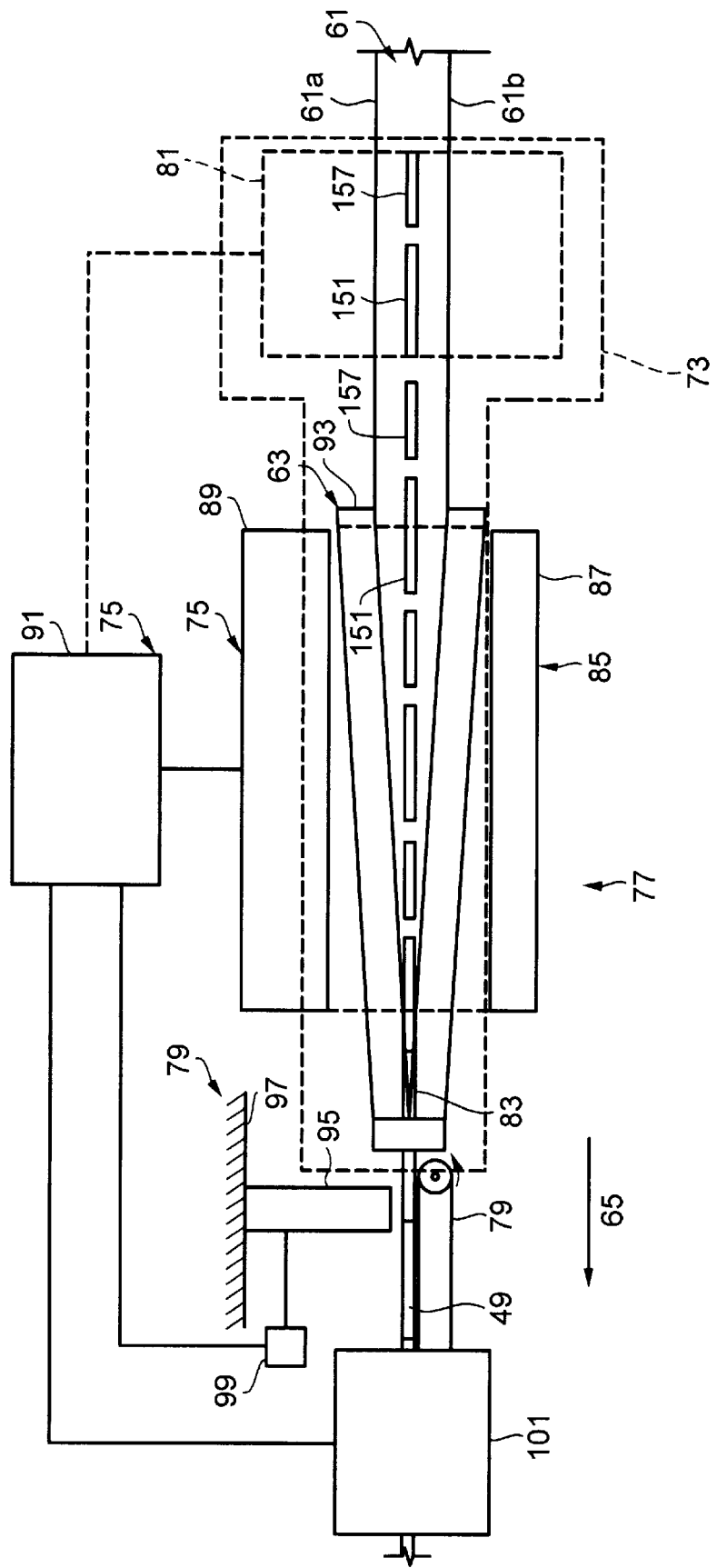
FIG. 5 is a schematic, top view of manufacturing equipment for a multi-component cigarette according to an embodiment of the present invention.

The cigarette 49 is preferably manufactured by streaming or introducing the components into a garniture device 63 as shown in FIG. 5. For the sake of simplicity of discussion and illustration, the components of the cigarette illustrated in FIG. 5 include only a tobacco rod 51, a space or void chamber 53, and a filter 57, along with the wrapper 61. Other components known to persons skilled in the art may also be included. The components are preferably introduced into a garniture device by feed wheels, which are preferably intermeshed spiral stock feeders which sequentially feed components onto the paper 61, which is preferably in web form and moved in a wrapping direction 65 for forming successive cigarettes. The paper 61 may be an essentially endless web, a web having the length of a predetermined number of cigarettes, such as four, or a web limited in length to a single cigarette.

In the cigarette of FIGS. 4 and 5, the paper 61 preferably includes a dual-layer wrapper. An external wrapper 67 is preferably paper, while an internal wrapper 69 is preferably a tobacco-containing wrapper, containing a form of processed tobacco sheet material. The tobacco rod 51 is preferably pre-wrapped by a paper wrapper 71 such that three wrapper layers surround the tobacco rod.

The apparatus 73 for combining the filter 57 with the wrapped tobacco rod 51 preferably has an "open" style garniture 63, i.e., one that does not close the internal and external wrappers 69 and 67 for at least one, preferably two or three, cigarette lengths. This open garniture 63 allows for a visual inspection of the component by an inspection arrangement 75.

The apparatus 77 for making and inspecting a multi-component cigarettes includes a device 79, such as spaced rollers or belts or vacuum rollers or belts, for advancing the paper 61, preferably in web form, in a first or wrapping direction 65. The advancing device 79 may include a portion disposed downstream of the garniture device 63 that operates by, for example, drawing the wrapped components between rollers or belts or drawing the wrapped components with a vacuum, and may also include a portion upstream from the garniture device, such as a motor for turning an axle upon which a roll of the paper 61 is wound to facilitate unwinding the paper.

The apparatus 77 further includes the combining apparatus 73 that positions the different components of the cigarette 49 relative to one another on the paper 61 as it is advanced in the wrapping direction 65 and wraps them together with the garniture device 63. The combining apparatus 73 preferably includes a positioning device 81 such as feed wheels 81, which are preferably intermeshed spiral stock feeders which sequentially feed components onto the paper 61 at some point upstream from the garniture device 63.

The garniture device 63 is arranged to wrap the paper 61 around the different components by causing the opposite edges 61a, 61b of the paper to be moved transversely to the first direction such that, at a closure point 83 in the garniture device 63, the opposite edges overlap each other to define a seam that is preferably sealed by an adhesive.

Figure 6:
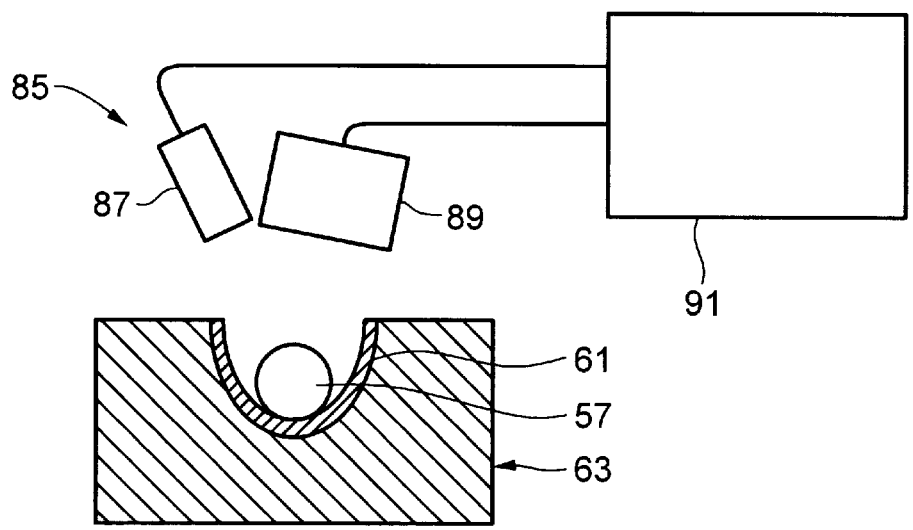
FIG. 6 is a schematic, cross-sectional view of manufacturing and inspection equipment for a multi-component cigarette, including an imaging device according to an embodiment of the present invention.

The inspection arrangement 75 includes an imaging device 85 disposed upstream of the closure point 83 of the garniture device 63. The imaging device 85 generates an image I of the different components. As seen in FIG. 6, the imaging device 85 preferably includes an illumination device 87 for illuminating the components. The illumination device 87 preferably includes a strobe light to facilitate generation of successive images of successive groups of the components, and the strobe light preferably includes a light emitting diode. The imaging device 85 preferably also includes an image acquiring or sensing device 89, such as a solid state CCD (charge coupled device) or MOS (metal oxide semiconductor) type television camera, for acquiring an image of the components illuminated by the illuminating device. U.S. Pat. No. 5,095,204 describes a machine vision inspection system suitable for use in connection with the present invention, and is hereby incorporated by reference.

Figure 7:
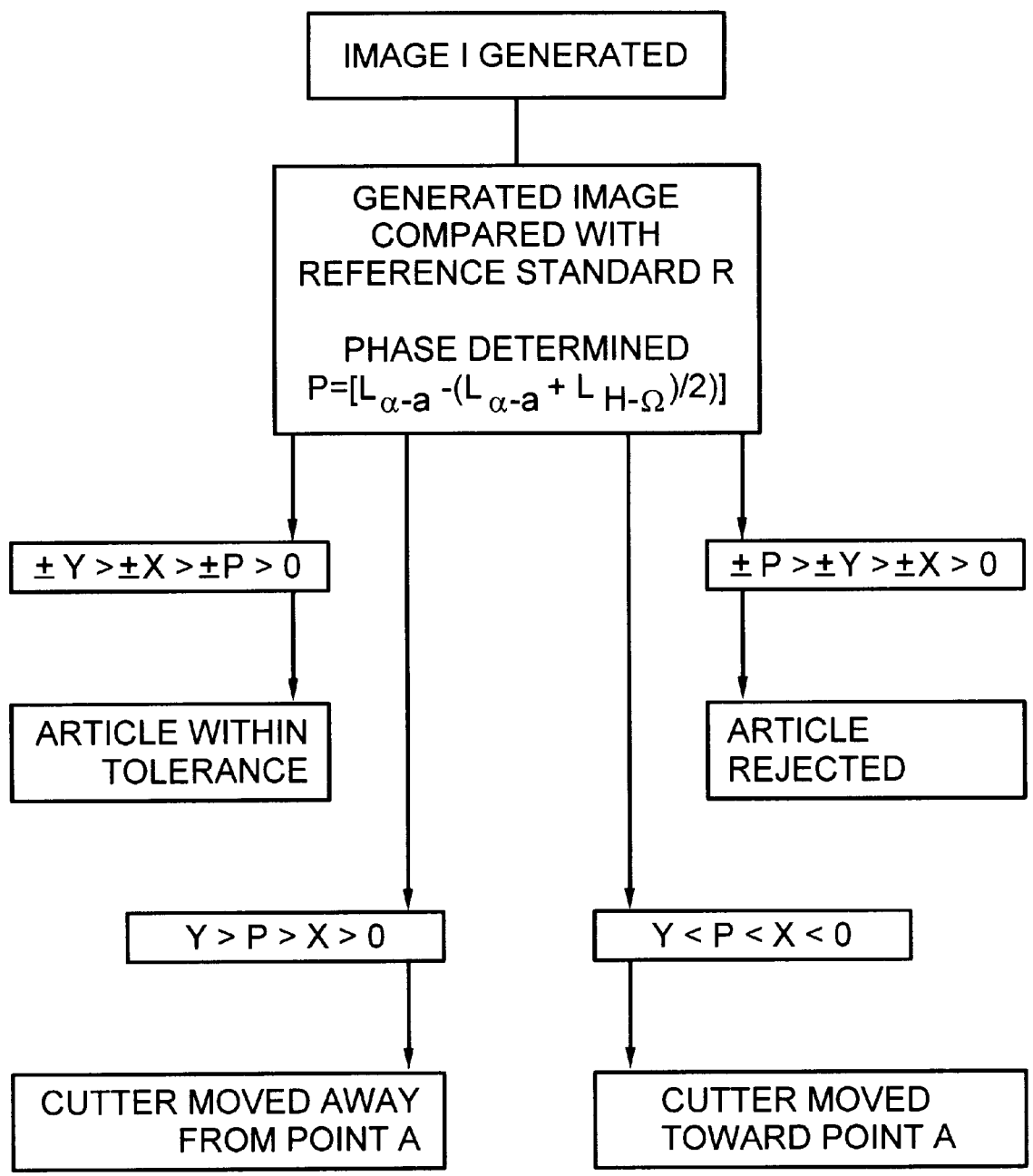
FIG. 7 is a flow diagram showing the steps of part of a manufacturing and inspection process according to an embodiment of the present invention.

As seen in FIG. 5, the inspection arrangement 75 further includes a processing or control device 91, such as a computer, connected to the imaging device 85 for comparing the generated image I with a reference standard R and determining if the generated image deviates from the reference standard as seen in the flow diagram of FIG. 7. The components of the cigarette 49 are preferably positioned relative to each other within certain tolerance ranges, and the components themselves are preferably sized to fall within certain tolerance ranges. If the generated image I deviates from the reference standard R, various remedial measures may be taken in response to a signal from the processing device.

Preferably, the positioning device 81 positions a plurality of the cigarette components relative to one another on a moving paper web 61 successively to permit production of cigarettes on a continuous basis. The length of the garniture device 63 from an upstream-most point 93 to the closure point 83 is preferably at least as long as a length from a leading end of a first one of the successively positioned components to a trailing end of a final one of the at least two components, such as a leading end of a filter 57 and a trailing end of a tobacco rod 51. The imaging device 85 is preferably disposed above the garniture device 63 and generates an image I of the components shortly before the paper 61 is wrapped around them. The imaging device 85 is, in any event, arranged relative to the garniture device 63 such that the imaging device generates an image I of the components from the leading end of the first one of the components to the trailing end of the final one of the two components.

In a particularly preferred embodiment, the different cigarette components positioned by the positioning device 81 include a double-length tobacco rod 151 and a double-length filter plug 157. The apparatus 77 preferably includes a cutting device 95, such as a rotating knife or a reciprocating guillotine, for cutting the double-length tobacco rod 151 and the double-length filter plug 157. The cutting device 95 is preferably adjustable, such as by movement of a blade along a track 97 by a drive 99 of the cutting device, to adjust the position or positions at which the double-length tobacco rod 151 and/or the double-length filter plug 157 are cut.

The processing device 91, or a separate device, such as a computer, preferably generates one or more signals in response to detection of a deviation of the generated image I from the reference standard R (see FIG. 7). The cutting device 95 is preferably responsive to the one or more signals from the processing device 91 to adjust the position of the cut of the double-length tobacco rod 151 and the double-length filter plug 157. The apparatus 77 preferably also includes a rejection device or station 101 operable in response to a signal from the processing device 91 to reject cigarettes 49 corresponding to a generated image I that the processing device determines to deviate by more than a predetermined amount from the reference standard R. The rejection device 101 may include, for example, a driven piston for pushing rejected cigarettes out of a stream of cigarettes made and inspected by the apparatus 77.

The illuminating device 87 is preferably a solid-state illuminating device that illuminates the components present in or preceding the garniture device. Light emitting diode arrays are particularly preferred to provide an even illumination. The arrays may provide a constant illumination, but are preferably "strobed" to trigger an image in the image acquiring device, such as a camera, the image is recorded and relayed to the processing device 91, such as a computer. Each time the camera is triggered, at least one single complete multi-component cigarette 49 is visible, preferably a four-cigarette length rod.

Figure 8:
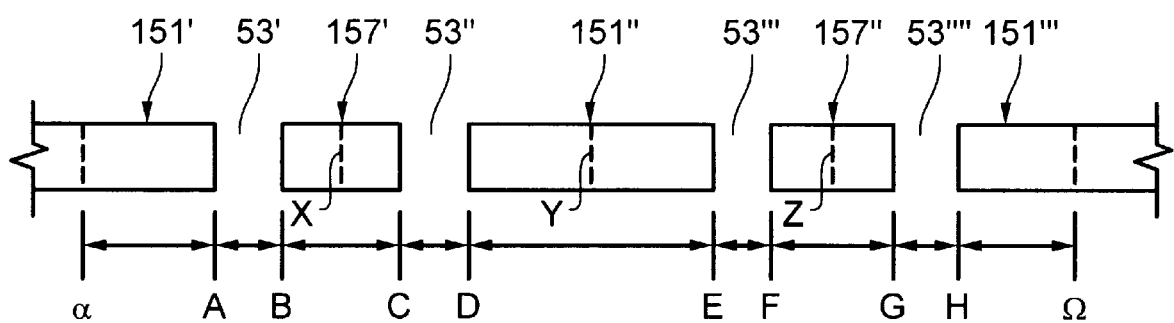
FIG. 8 is a schematic, top view of an image of a multi-component cigarette generated by an imaging device of a manufacturing and inspection apparatus according to an embodiment of the present invention.

FIG. 8 shows a multi-component image I. A portion of a double-length tobacco rod 151' is visible extending from point a to point A. A void 53' extends from point A to point B; a double-length filter tip 157' extends from points B to C; a subsequent void 53" extends from points C to D; a subsequent double-length tobacco rod 151" extends from points D to E; another subsequent void 53''' extends from points E to F; a subsequent double-length filter tip 157" extends from points F to G; a further subsequent void 53"" extends from points G to H; a portion of a further subsequent double-length tobacco rod 151''' extends from points H to Ω; with the arrangement of components continuing on in the same manner back to the positioning device (FIG. 5).

In a preferred embodiment, the components extending from α to Ω are visible to the imaging device 85. Assuming point α is in the middle of tobacco rod 51' and point Ω is in the middle of tobacco rod 51''', the rod being inspected is the precursor of four multi-component cigarettes, ultimately being cut at points α, x, y, z, and Ω by the cutting device 95.

A preferred embodiment of this invention uses the components from points α to Ω as the image locator. Lengths α to A and H to Ω preferably each measure a particular amount: preferably from 10–80 mm; more preferably from about 10–30 mm; and still more preferably about 10 mm. Lengths A to B, C to D, E to F, and G to H preferably each measure from 2–15 mm, more preferably 5–10 mm, and still more preferably about 7 mm. Lengths B to C and F to G preferably each measure from 8–22 mm, more preferably from 10–20 mm, and still more preferably about 14 mm. Length D to E preferably measures from 20–160 mm, more preferably about 30–60 mm, and still more preferably about 36 mm.

The processing device 91 preferably processes the image generated by the imaging device 85 and performs a simple image measurement to yield the measurement values of the components imaged and their relative placement. Utilizing these image measurements, a single calculation can be used to adjust cutting points x, y, and z to ensure tolerances are met to.

The cutting device 95 can be "phased" to keep components properly oriented by relocating, e.g., a cutting point of a blade or blades of the cutting device relative to the components according to, for example, the following formula:

Phasing $(P)=[L_{\alpha-a}-(L_{\alpha-a}+L_{H-\Omega})/2)]$

According to this formula, and as seen in FIG. 7, when P=0 or is between ±X (some predetermined tolerance limit), no blade adjustment is required. If P>X>0, the processing device 91 sends a signal to the cutting device 95 to advance away from point A. If P<X<0, the processing device 91 sends a signal to the cutting device to advance toward point A. It may also occur that P is so large, e.g., outside of ±Y, that adjustment of the location of the blade cannot compensate for the problem. In this case, the processing device 91 can send a signal to the rejection device 101 to reject the out-of-tolerance cigarette.

Other inspections, such as to determine if color is off, if foreign matter is detected, or if components are misshapen or misplaced, are identified and tracked by registration and rejected later in the system, preferably by the rejection device 101.

In a method for making and inspecting a multi-component cigarettes 49 according to the present invention, the paper web 61 is advanced by the advancing device in the first or wrapping direction 65. Different components, such as the tobacco rod 51, the acetate tube 55, and the filter 57, of the cigarette 49 are positioned relative to one another on the web 61 by the positioning device 81 as the web advances in the first direction 65, preferably in a successive manner to permit formation of successive cigarettes. The web 61 is wrapped around the different components by moving opposite edges 61a and 61b of the web transversely to the first direction with a garniture device 63 such that, at a closure point 83 in the garniture device, the opposite edges overlap each other.

An image I (FIGS. 7 and 8) of the different components is generated with an imaging device 85 disposed upstream of the closure point 83 and, preferably, above the garniture device 63. The generated image I is compared with a reference standard R with a processing device 91, and the processing device determines if the generated image deviates from the reference standard. The components of the cigarette are preferably illuminated with an illuminating device 87, preferably a strobe light, in connection with the generation of the image by the imaging device 85. In generating the image with the imaging device 85, the image I of the components illuminated by the illuminating device 87 is preferably acquired with an image acquiring device 89.

Preferably, the different components positioned relative to one another by the positioning device 81 include a double-length tobacco rod 151 and a double-length filter plug 157. The double-length tobacco rod 151 and the double-length filter plug 157 are cut by the cutting device 95.

When the processing device 91 detects a deviation of the generated image I from the reference standard R, it preferably generates one or more signals in response to the detection, the signals being received by the cutting device 95 which adjusts a position of a cut (e.g., x, y, and/or z in FIG. 8) of at least one of the double-length tobacco rod 151 and the double-length filter plug 157 in response to the one or more signals. When a generated image I is determined deviate by more than a predetermined amount from the reference standard R, the processing device 91 preferably generates a signal to which the rejection device is responsive, and the rejection device rejects cigarettes corresponding to the generated image.

While this invention has been illustrated and described in accordance with a preferred embodiment, it is recognized that variations and changes may be made therein without departing from the invention as set forth in the claims.

What is claimed is:

1. A method for making and inspecting a multi-component cigarettes, each cigarette including two or more different components arranged relative to one another, comprising the steps of:
   advancing a web in a first direction;
   positioning at least two different components of a cigarette relative to one another on the web as the web advances in the first direction;
   wrapping the web around the at least two different components by moving opposite edges of the web transversely to the first direction with a garniture device such that, at a closure point in the garniture device, the opposite edges overlap each other;
   generating an image of the at least two different components with an imaging device disposed upstream of the closure point; and
   comparing the generated image with a reference standard and determining if the generated image deviates from the reference standard with a processing device.

2. The method as set forth in claim 1, wherein the at least two different components positioned relative to one another include a tobacco rod and a filter plug.

3. The method as set forth in claim 2, wherein the tobacco rod and the filter plug are positioned relative to each other such that an end of the tobacco rod and a closest end of the filter plug are disposed at a distance from each other.

4. A The method as set forth in claim 1, wherein the at least two different components positioned relative to one another include a tobacco rod, a tube, and a filter plug.

5. The method as set forth in claim 4, wherein the tobacco rod, the tube, and the filter plug are positioned relative to each other such that an end of the tobacco rod is adjacent a first end of the tube, and a second end of the tube is disposed at a distance from a closest end of the filter plug.

6. The method as set forth in claim 1, wherein the imaging step includes illuminating the at least two components with an illuminating device.

7. The method as set forth in claim 6, wherein the at least two components are illuminated with a strobe light.

8. The method as set forth in claim 1, wherein the imaging step includes acquiring an image of the components illuminated by the illuminating device with an image acquiring device.

9. The method as set forth in claim 1, wherein the positioning step includes positioning a plurality of the at least two components relative to one another on the moving web successively.

10. The method as set forth in claim 9, wherein the at least two different components positioned relative to one another include a double-length tobacco rod and a double-length filter plug, the method comprising the further steps of cutting the double-length tobacco rod and the double-length filter plug.

11. The method as set forth in claim 10, comprising the further steps of generating one or more signals in response to detection of a deviation of the generated image from the reference standard, and adjusting a position of a cut of at least one of the double-length tobacco rod and the double-length filter plug in response to the one or more signals.

12. The method as set forth in claim 11, comprising the further step of generating a signal with the processing device when a generated image is determined deviate by more than a predetermined amount from the reference standard, and rejecting cigarettes corresponding to the generated image with a rejection device operable in response to the signal.

13. The method as set forth in claim 1, comprising the further steps of generating a signal with the processing device when a generated image is determined deviate by more than a predetermined amount from the reference standard, and rejecting cigarettes corresponding to the generated image with a rejection device operable in response to the signal.

14. A method of making and inspecting a multi-component article, comprising the steps of:
arranging a plurality of components relative to one another;
generating an image of the arranged components with an imaging device;
comparing the generated image with a reference standard; and
determining if the generated image deviates from the reference standard.

15. The method as set forth in claim 14, comprising the further step of wrapping the components in a wrapping material, wherein the components are arranged relative to one another on the wrapping material prior to wrapping.

16. The method as set forth in claim 15, wherein the components include at least one tobacco rod and at least one filter element.

17. The method as set forth in claim 16, wherein each of the components are separated from another one of the components by a gap.

18. The method as set forth in claim 14, comprising the further step of wrapping the components in a wrapping material in a continuous wrapping operation, wherein the wrapping material is moved in a wrapping direction and the components are arranged relative to one another on the wrapping material prior to wrapping as the wrapping material is moved in the wrapping direction.

19. The method as set forth in claim 18, wherein the wrapping material is wrapped around the components in a direction transverse to the wrapping direction.

20. The method as set forth in claim 18, wherein the components include at least one tobacco rod and at least one filter element.

21. The method as set forth in claim 20, wherein each of the components are separated from another one of the components by a gap.

22. The method as set forth in claim 20, wherein the continuous wrapping operation produces successive wrapped sets of components, the method comprising the further step of separating the successive wrapped sets of components from one another to form a finished article.

23. The method as set forth in claim 22, wherein successive wrapped sets of components are separated from one another by a cutting device.

24. The method as set forth in claim 14, comprising the further steps of generating a signal when the generated image and the reference standard deviate, and identifying components corresponding to the generated image that deviate from the reference standard in response to the signal.

25. The method as set forth in claim 24, comprising the further step of wrapping the components in a wrapping material in a continuous wrapping operation, the continuous wrapping operation produces successive wrapped sets of components, and separating the successive wrapped sets of components from one another to form a finished article.

26. The method as set forth in claim 25, comprising the further step of rejecting finished articles including components identified as deviating from the reference standard.

27. The method as set forth in claim 24, wherein the components are wrapped in an open garniture wrapping device.

28. The method as set forth in claim 27, wherein the successive wrapped sets of components are separated from one another by a cutting device.

29. The method as set forth in claim 14, wherein the image of the components is generated by illuminating the components and acquiring an image of the illuminated components.

30. The method as set forth in claim 29, comprising the further step of wrapping the components in a wrapping material in a continuous wrapping operation, and wherein the components are illuminated with a strobe light.

* * * * *